United States Patent
Kim (10) Patent No.: US 7,357,028 B2
(45) Date of Patent: Apr. 15, 2008

(54) NONDESTRUCTIVE TESTING APPARATUS

(75) Inventor: Sung Kim, Busan (KR)

(73) Assignee: Mi Sung C & S Inspection Co., Ltd, Basan (KR)

( * ) Notice: Subject to any disclaimer, the term of this patent is extended or adjusted under 35 U.S.C. 154(b) by 134 days.

(21) Appl. No.: 11/152,870

(22) Filed: Jun. 15, 2005

(65) Prior Publication Data

US 2006/0230832 A1  Oct. 19, 2006

(30) Foreign Application Priority Data

Apr. 15, 2005  (KR) .................. 10-2005-0031415

(51) Int. Cl.
*G01N 29/24* (2006.01)

(52) U.S. Cl. .................. 73/627; 73/628; 73/641; 73/786

(58) Field of Classification Search .................. 73/627, 73/628, 640, 641, 786
See application file for complete search history.

(56) References Cited

U.S. PATENT DOCUMENTS

| | | | | | |
|---|---|---|---|---|---|
| 5,122,991 | A | * | 6/1992 | Koike et al. | 367/127 |
| 5,675,085 | A | * | 10/1997 | Hayashi et al. | 73/628 |
| 6,003,376 | A | * | 12/1999 | Burns et al. | 73/584 |
| 6,298,726 | B1 | * | 10/2001 | Adachi et al. | 73/632 |
| 6,584,847 | B1 | * | 7/2003 | Hirose | 73/579 |

\* cited by examiner

*Primary Examiner*—Hezron Williams
*Assistant Examiner*—Jacques M. Saint-Surin
(74) *Attorney, Agent, or Firm*—David W. Carstens; Carstens & Cahoon, LLP (57) ABSTRACT

A nondestructive testing apparatus inspects an internal part of a large-diameter pile using both a single transmission/reception probe for transmitting/receiving an ultrasound signal of more than 50 kHz and a plurality of reception probes, digitally processes the received frequency, and outputs the inspected result.

2 Claims, 11 Drawing Sheets

< Analog signal reception system >

< Digital reception system >

FIG. 7

NONDESTRUCTIVE TESTING APPARATUS

BACKGROUND OF THE INVENTION

1. Field of the Invention

The present invention relates to a nondestructive testing apparatus, and more particularly to a nondestructive testing apparatus capable of testing quality of a large-sized structural concrete partition buried in the seabed or in the earth, for example, a large-diameter placing pile, and Caisson line, etc.

2. Description of the Related Art

With increasing industrialization, fundamental components indicative of large-sized structures, such as bridges and harbors, have been rapidly increased. The above-mentioned bridge or harbor structure may collapse if unexpected holes occur during a curing period for a concrete pile contained in the structure, such that the necessity of estimating if the structure is in a normal state has been rapidly increased.

There have been widely used first to third methods to estimate if the structure is in a normal state. In the case of the first method, a user excavates peripheral parts of a concrete pile, and inspects the presence or absence of damage of the concrete pile and the position of the damage. In the case of the second method, a user strikes the concrete pile with a hammer, detects elastic waves using a specific sensor, and inspects the presence or absence of damage of the concrete pile and the position of the damage on the basis of the shape of the elastic waves. In the case of the third method, a user performs core boring of the concrete pile, measures the concrete pile and its peripheral displacement using a clinometer, and inspects the presence or absence of damage of the concrete pile and the position of the damage.

However, the first method, in which the user performs excavation and views the damage of the concrete pile, requests a large-sized excavating operation, such that it requires large-scale equipment, and consumes an unnecessary long period of time and great cost. The second method using the elastic waves has poor precision, such that it must be used along with the above-mentioned first method at the same time. The third method using the clinometer requires boring, such that it consumes an unnecessary long period of time and great cost.

Figure 1A:
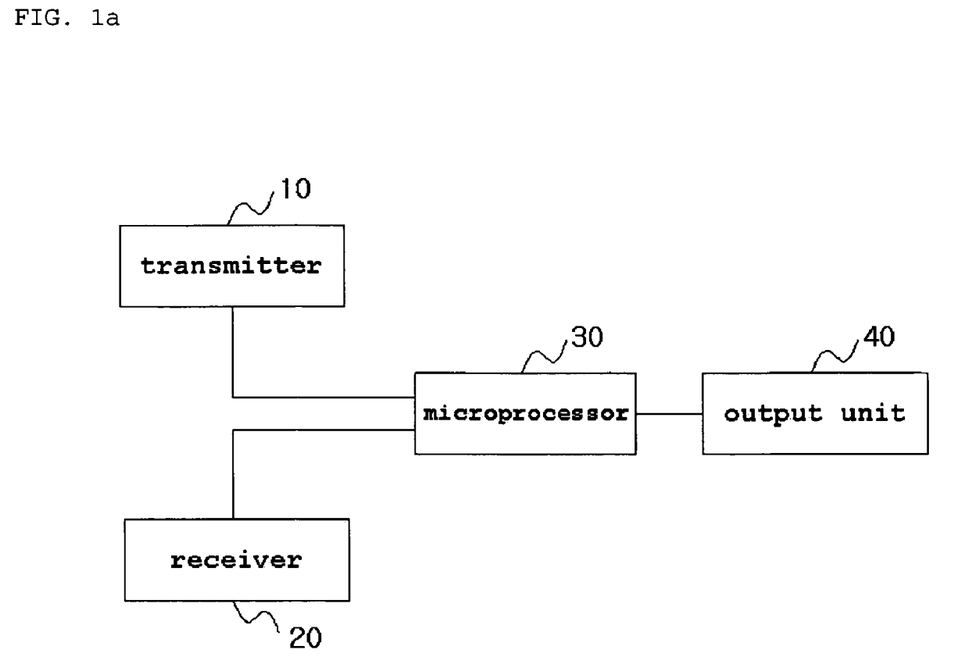
FIGS. 1a~1b are block diagrams illustrating a conventional nondestructive testing apparatus.
Figure 1B:
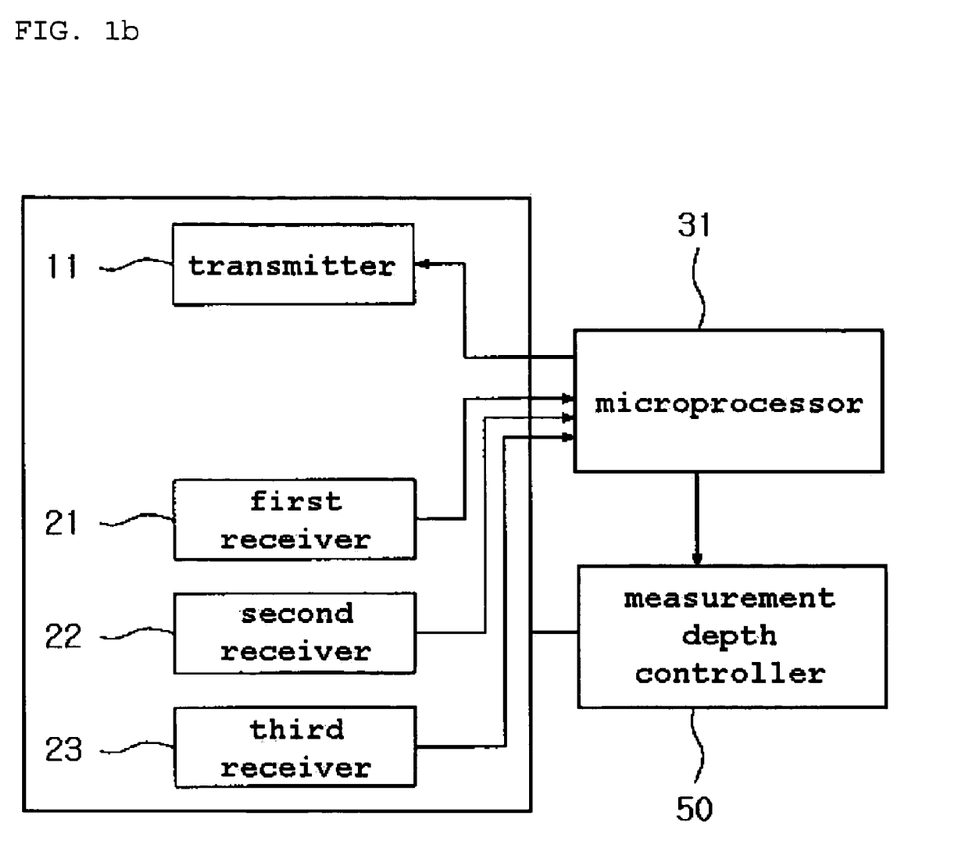

In order to above-mentioned problems, a nondestructive testing apparatus shown in FIGS. 1a~1b is developed.

Figure 1C:
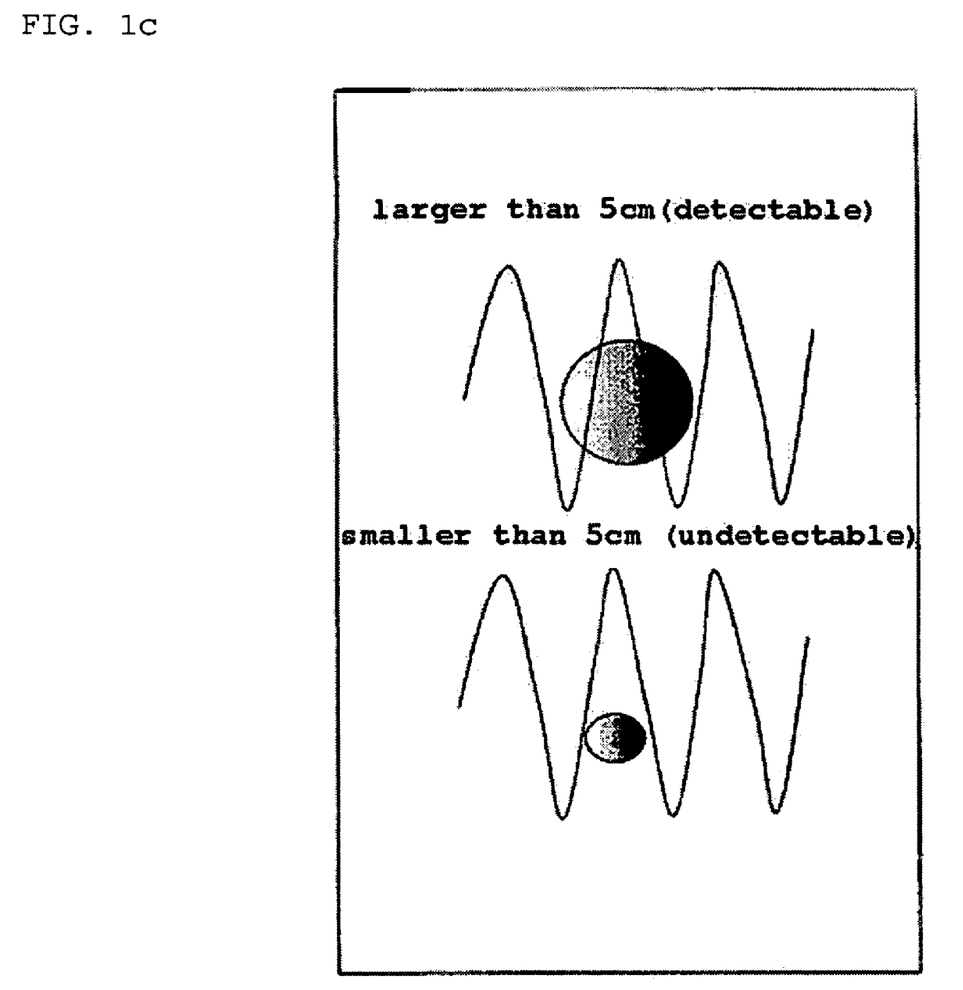
FIG. 1c shows a conventional method for detecting a defect using ultrasound.
Figure 1D:
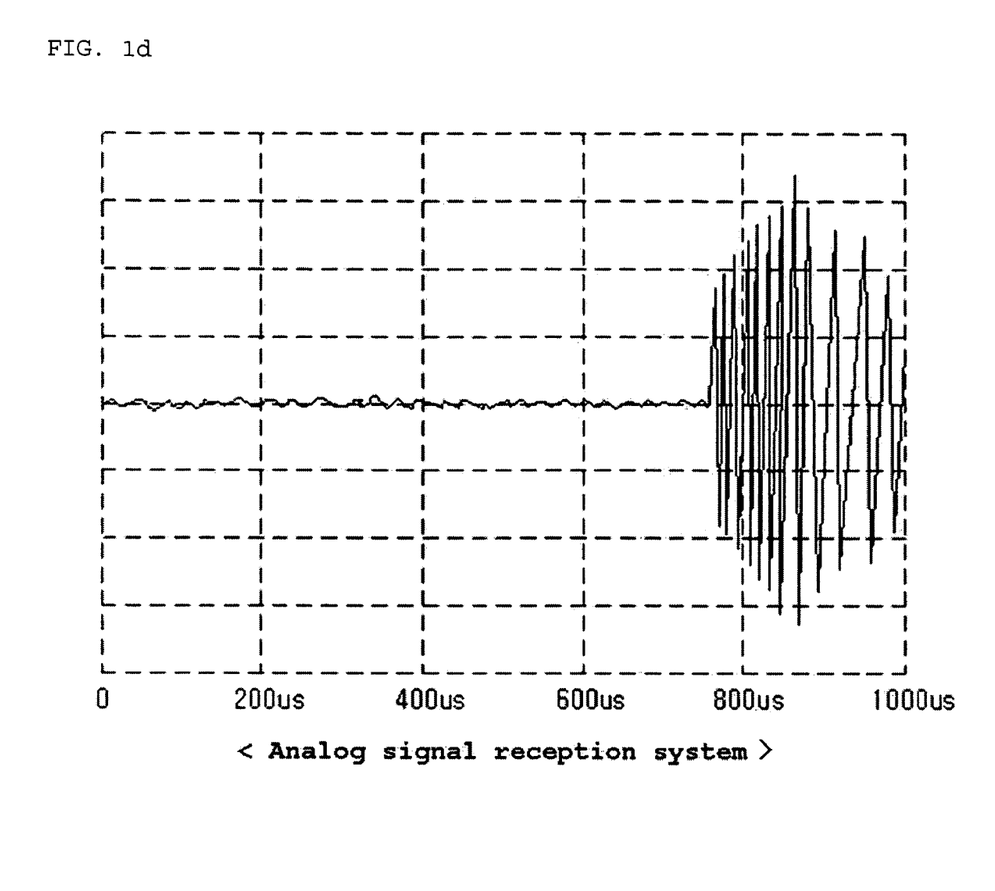
FIG. 1d shows an example for illustrating a reception system problem encountered when the conventional nondestructive testing apparatus is used.

FIGS. 1a~1b show block diagrams illustrating a conventional nondestructive testing apparatus. FIG. 1c shows a conventional method for detecting a defect using ultrasound. FIG. 1d shows an example for illustrating a reception system problem encountered when the conventional nondestructive testing apparatus is used.

The conventional nondestructive testing apparatus shown in FIG. 1a includes a transmitter 10 for generating one-way ultrasound; a receiver 20 for receiving the ultrasound from the transmitter 10; a microprocessor 30 for generating a control signal to control the transmitter 10 to generate the ultrasound, receiving ultrasound information from the receiver 20, analyzing the received ultrasound information, and determining the presence or absence of internal quality abnormality of the concrete pile; and an output unit 40 for printing out the determined result of the microprocessor 30 or displaying the same determined result on a screen.

In this case, the nondestructive testing apparatus shown in FIG. 1a connects the transmitter 10 to the receiver 20 on a one to one basis, such that it requires a plurality of transmission and reception processes to perform overall quality testing. Also, the nondestructive testing apparatus entirely depends on a manual operation of a user who carries out the nondestructive testing, such that reliability of the quality testing result is deteriorated if the user is unskilled at the quality testing or makes an unexpected mistake. Also, the user must hold the transmitter 10 and the receiver 20, or must attach the same to a necessary part, such that it has difficulty in performing the above-mentioned testing on inaccessible areas such as the seabed and the subterranean parts.

In order to solve the above-mentioned problem, a nondestructive testing apparatus shown in FIG. 1b has been developed. The nondestructive testing apparatus shown in FIG. 1b includes a transmitter 11 inserted in a vertical hole to generate ultrasound in a radial direction of 360°; a plurality of receivers 21, 22, and 23 inserted in vertical holes different from the vertical hole of the transmitter 11 at the same depth to receive the ultrasound from a concrete partition; a measurement depth controller 500 for allowing the transmitter 11 and the receivers 21~23 to maintain the same depth; and a microprocessor 31 for analyzing speed of the ultrasound received from the receivers 21~23 according to an internal program, determining density and quality of concrete, and displaying the determined density and quality of the concrete.

In this case, although the nondestructive testing apparatus shown in FIG. 1b is able to perform an overall quality test of the structure using only one transmission/reception process, it uses a low frequency of about 50 kHz as a transmission frequency, such that it is unable to recognize a defect of the structure. The conventional nondestructive testing apparatus shown in FIGS. 1a~1b may encounter the following first to third problems.

According to the first problem, the conventional nondestructive testing apparatus cannot detect small-sized defects of less than a predetermined size. A resonance frequency 50 kHz of a transmission probe (i.e., a transmitter) of each conventional nondestructive testing apparatus based on the conventional ITS-2002 specification controls its own waveform to have a wavelength of 8 cm when speed of ultrasound passing through the concrete is 4,000 m/sec. Generally, the size of each internal defect contained in the concrete is bigger than the 8 cm, such that there is no need to detect a small-sized defect less than the 8 cm. As such, nondestructive testing apparatuses employing the above-mentioned frequency band have rapidly come into widespread use. However, as the number of large-sized structures is rapidly increased, small aggregate of less than 5 cm is used as specific aggregate (e.g., gravel or crushed aggregate) capable of maintaining high strength of the structure, and the use of the small aggregate less than 5 cm is commercially available. It is impossible for the transmission/reception probe for use in the conventional concrete nondestructive testing apparatus to detect an internal defect (e.g., a cold joint) of the concrete of less than 5 cm. In other words, in order to detect a small-sized concrete internal defect such as a cold joint considered to be an important matter in a construction site, a frequency range of a transmission/reception probe must be extended to 50 kHz~400 kHz and over, but it should be noted that a current transmission/reception probe has yet to overcome the above-mentioned limitation.

According to the second problem, the conventional nondestructive testing apparatus cannot recognize a defect in three dimensions. In other words, a transmission probe of the conventional nondestructive testing apparatus receives ultrasound, and a reception probe thereof receives ultrasound having passed through an internal medium of the concrete. Therefore, a user compares an initial ultrasound arrival time in a normal concrete medium with the other initial ultrasound arrival time in a defective medium, determines the size of the defect, and reports the defect to the person in charge, such that the user can predict type and shape information of the defect. However, the above method requires analysis of th upper/lower homogeneity of the concrete using the logging of the transmission/reception probes, and requires analysis of data of a reception point at different vertical distance transmission locations using the same logging, such that it has difficulty in measuring position and size information of a concrete defect oriented vertically in a large-diameter pile. In order to measure the position and size of the defect contained in the concrete, a plurality of measurement holes must be buried before constructing the large-diameter pile, resulting in consumption of an unnecessarily long period of time and great cost. The conventional nondestructive testing apparatus analyzes the data obtained by the above-mentioned process, and predicts only the size of the defect contained in the concrete, such that it is unable to measure at least two-dimensional result.

According to the third problem, the conventional nondestructive testing apparatus is configured in the form of an analog signal reception system as shown in FIG. 1d, such that its inspection function is limited. In other words, a transmission probe for use in the conventional nondestructive testing apparatus generates a resonance frequency of 50 kHz, and uses a long wavelength due to the resonance frequency of 50 kHz, such that the conventional nondestructive testing apparatus is unable to predict a small defect contained in the concrete whereas it has a very long ultrasound measurement distance. Also, the conventional nondestructive testing apparatus has a limitation in performing a gain control operation. For example, provided that speed of ultrasound passing through the concrete is 4,000 m/sec, an initial ultrasound arrival time is shown in the following Table 1.

TABLE 1

| Ultrasound Time During Passing 1M | 250 μs |
|---|---|
| Ultrasound Time During Passing 2M | 500 μs |
| Ultrasound Time During Passing 3M | 750 μs |

In this case, a signal display unit for use in a conventional concrete nondestructive testing apparatus using an analog signal controls an ultrasound frequency to be adjacent to a predetermined frequency of 50 kHz, each of all time divisions for use in the nondestructive testing apparatus is limited to 200 μs, and an overall time division associated with a horizontal axis of an analog reception signal is divided into five stages, such that a maximum width may be denoted by 200 μs×5=1000 μs. As a result, the initial ultrasound arrival time denoted by the waveform shown in FIG. 1d is generated in almost the last part of the waveform, such that the conventional nondestructive testing apparatus has difficulty in analyzing reception data.

In conclusion, the above-mentioned conventional analog-type concrete nondestructive testing apparatus widely used to inspect large-diameter piles fixes an overall time division to 1000 μs, such that an initial waveform is slightly generated in the last part of a display when testing defective concrete. As a result, the above-mentioned nondestructive testing apparatus is unable to measure a horizontal length of the defect and energy variation. In addition, if the width of the concrete structure is increased, the size of the time division is higher than 1000 μs, such that the nondestructive testing apparatus is unable to detect concrete defects.

SUMMARY OF THE INVENTION

Therefore, the present invention has been made in view of the above problems, and it is an object of the invention to provide a nondestructive testing apparatus for inspecting an internal part of a large-diameter pile using a single transmission/reception probe capable of transmitting/receiving ultrasound of more than 50 kHz and a plurality of reception probes, digitizing a received frequency, and outputting the inspection result.

In accordance with the present invention, the above and other objects can be accomplished by the provision of a nondestructive testing apparatus, comprising: a transmission/reception probe which is inserted into a hole formed in a partition of a concrete structure, generates ultrasound of more than 50 KHz in a radial direction of 360°, and receives the reflected ultrasound after the ultrasound is reflected; a plurality of reception probes inserted in vertical holes different from that of the transmission/reception probe at the same depth in order to receive the ultrasound from the concrete partition; a measurement depth controller for allowing the transmission/reception probe and the reception probes to maintain the same depth; a microprocessor for controlling the measurement depth controller, converting information of the ultrasound received from the transmission/reception probe and the reception probes into digital ultrasound information, analyzing the digital ultrasound information, and determining density and quality of the concrete structure; and an output unit for displaying various information analyzed by the microprocessor to allow a user to view the displayed information, and outputting the analyzed information.

BRIEF DESCRIPTION OF THE DRAWINGS

The above objects, and other features and advantages of the present invention will become more apparent after reading the following detailed description when taken in conjunction with the drawings, in which.

DESCRIPTION OF THE PREFERRED EMBODIMENTS

Now, preferred embodiments of the present invention will be described in detail with reference to the annexed drawings. In the drawings, the same or similar elements are denoted by the same reference numerals even though they are depicted in different drawings. In the following description, a detailed description of known functions and configurations incorporated herein will be omitted when it may make the subject matter of the present invention rather unclear.

Figure 2:
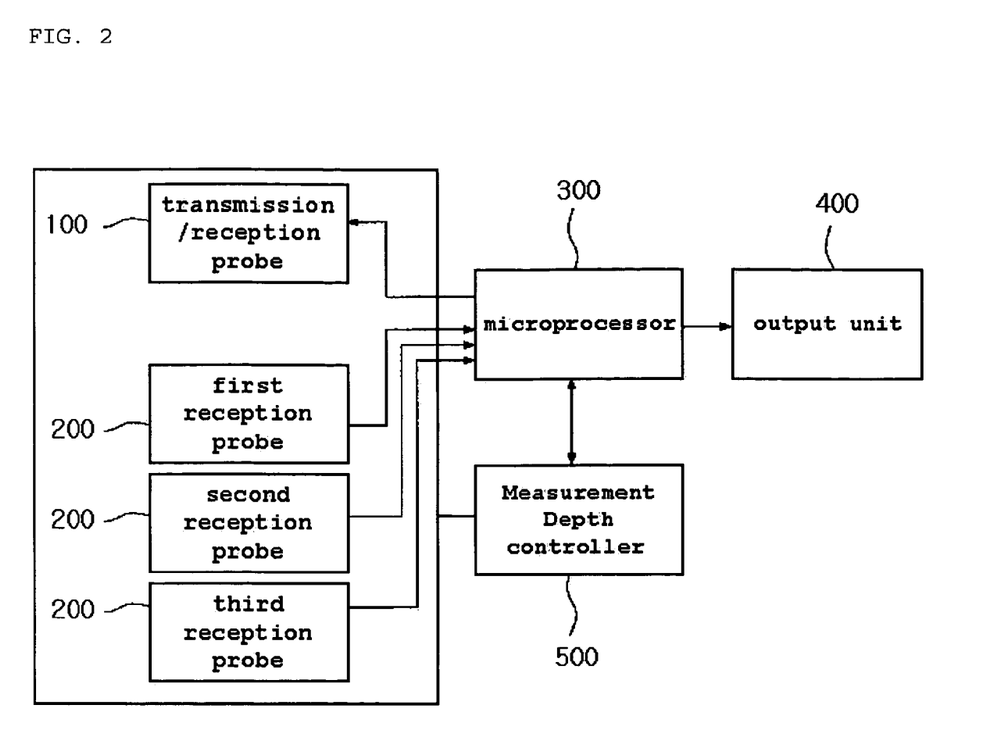
FIG. 2 is a block diagram illustrating a nondestructive testing apparatus according to the present invention.
Figure 3A:
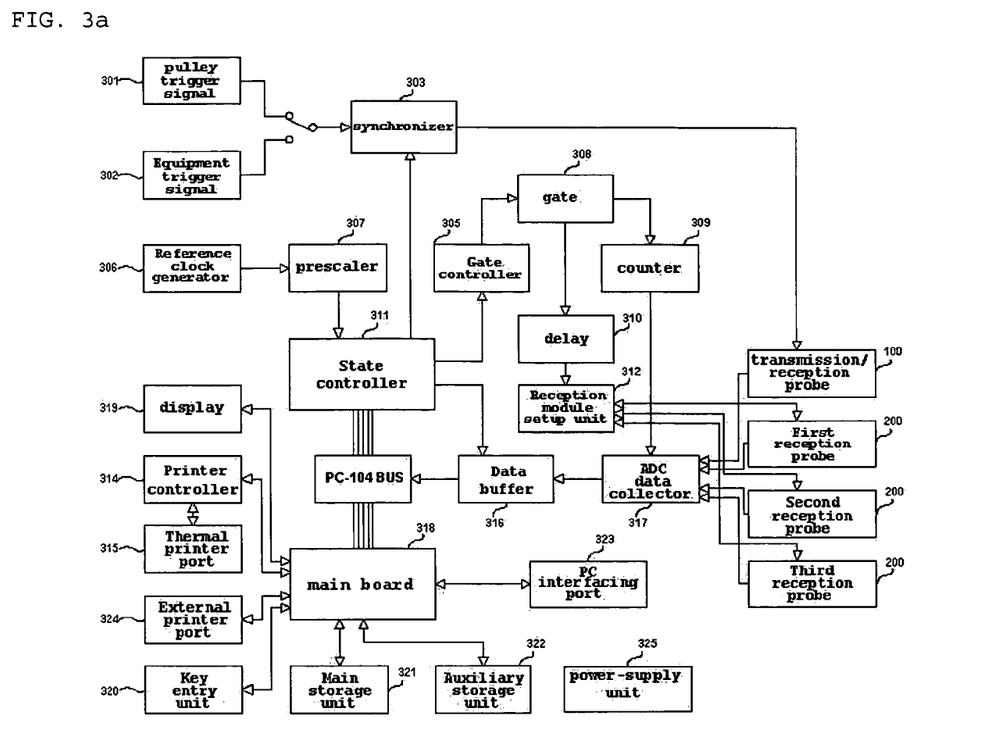
FIG. 3a is a block diagram illustrating a microprocessor according to the present invention.
Figure 3B:
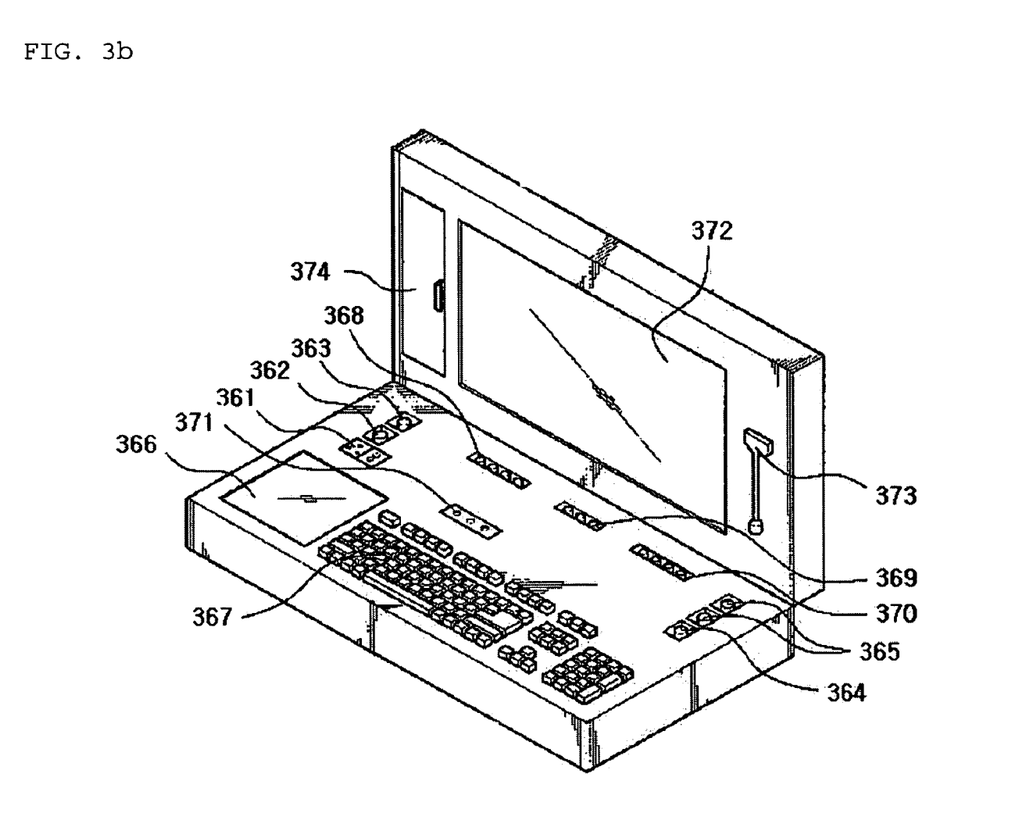
FIG. 3b shows the appearance of an exemplary microprocessor according to the present invention.
Figure 4:
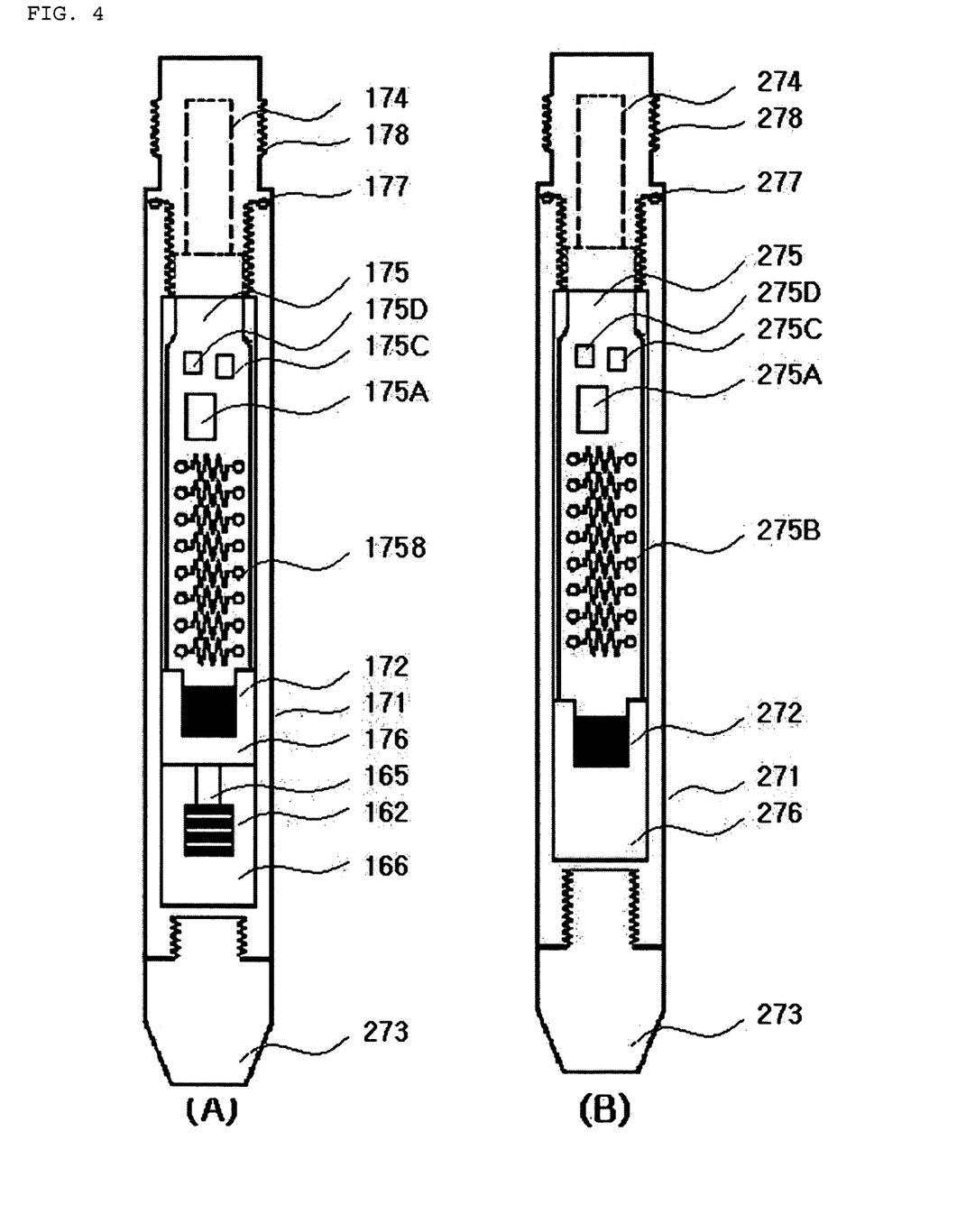
FIG. 4 shows internal configurations of a transmission/reception probe and a reception probe according to the present invention.

FIG. 2 is a block diagram illustrating a nondestructive testing apparatus according to the present invention. FIG. 3a is a block diagram illustrating a microprocessor according to the present invention. FIG. 3b shows the appearance of an exemplary microprocessor according to the present invention. FIG. 4 shows internal configurations of a transmission/reception probe and a reception probe according to the present invention.

In order to use the nondestructive testing apparatus shown in FIG. 2 according to the present invention, a plurality of vertical holes must be formed in a concrete structure such as a large-sized structural concrete partition, for example, a large-diameter placing pile, and Caisson line, etc.

The nondestructive testing apparatus shown in FIG. 2 includes a transmission/reception probe 100 inserted in a vertical hole to generate ultrasound in a radial direction of 360°, and receiving the reflected ultrasound; a plurality of reception probes 200 inserted in vertical holes different from that of the transmission/reception probe 100 at the same depth in order to receive the ultrasound from the concrete partition; a measurement depth controller 500 for allowing the transmission/reception probe 100 and the reception probes 200 to maintain the same depth; a microprocessor 300 for controlling the measurement depth controller 500, converting ultrasound information received from the transmission/reception probe 100 and the reception probes 200 into digital ultrasound information, analyzing the digital ultrasound information, and determining density and quality of concrete; and an output unit 400 for displaying various information analyzed by the microprocessor 300 to allow a user to view the displayed information, and outputting the analyzed information. In this case, the output unit 400 may be a display or a printer, and may be integrated with the microprocessor 300 or may also be separated from the microprocessor 300.

The internal components of the microprocessor 300 are shown in FIG. 3a. As shown in FIG. 3a, reference numeral 303 indicates a synchronizer. The synchronizer 303 selectively receives either a pulley trigger signal 301 which can determine a predetermined point to be inspected, or an equipment trigger signal 302 generated from an internal part of equipment, and synchronizes the selected trigger signal with an internal reference clock. In this case, the pulley trigger signal 301 has different scanning depths (e.g., 1.25 cm, 2.5 cm, and 5 cm, etc) according to setup information of a state controller 311. If the equipment trigger signal 302 has an output signal of about 10 MHz, an optimum result may be predicted.

Reference numeral 100 indicates the transmission/reception probe for substantially generating ultrasound according to a control signal of the state controller 311. Reference numeral 305 indicates a gate controller for controlling an output signal of a prescaler 307 using a trigger signal synchronized by the synchronizer 303. Reference numeral 306 indicates a reference clock generator for generating a clock signal of 8 MHz acting as a reference of equipment operation. Reference numeral 307 indicates a prescaler 307. The prescaler 307 prescales the reference clock generated from the reference clock generator 306, and generates a conversion start signal to be transmitted to an ADC of the reception probe 200. In this case, operations of the prescaler 307 may be user programmable.

Reference numeral 308 indicates a gate for transmitting or cutting off the output signal of the prescaler 307 upon receiving a control signal from the gate controller 305. Reference numeral 309 indicates a counter capable of determining the number of data units to be collected by the reception probe 300. Reference numeral 310 indicates a delay capable of adjusting inconsistency between an ultrasound output signal of the transmission/reception probe 100 and an operation time of each reception probe 200. In this case, it is preferable that the counter 309 sets the number of data units to be collected to 384, and the delay 310 removes a time error generated when a digital signal passes individual circuit units.

Reference numeral 311 indicates a state controller. The state controller 311 inspects a current operation state of the equipment, establishes operations of the transmission/reception probe 100 and the reception probe 200, and establishes a scanning interval of a pulley. Reference numeral 312 indicates a reception module setup unit for establishing state information to operate the reception probe 200. Reference numeral 200 indicates a reception probe, which receives ultrasound generated from the transmission/reception probe 100 at intervals of a predetermined time determined by the prescaler 307, and collects data.

Reference numeral 314 indicates a printer controller for performing various control operations of an output signal of a thermal printer (i.e., the output unit 400) used to output data in an inspection field. Reference numeral 314 indicates a thermal printer port connected to the thermal printer (i.e., the output unit 400). Reference numeral 318 indicates a main board for performing calculation and controlling individual system components.

Reference numeral 317 indicates an ADC (Analog-to-Digital Conversion) data collector which receives control signals from the state controller 311 and the counter 309, and converts ultrasound signals detected by the transmission/reception probe 100 and the reception probe 200 into a digital signal. Reference numeral 316 indicates a data buffer, which connects a data bus, and transmits a digital signal received from the ADC data collector 317 to a main board 318 according to a control signal of the state controller 311.

Reference numeral 319 indicates a display using a 10.4-inch LCD panel (i.e., the output unit 400). Reference numeral 320 indicates a key entry unit for receiving a control signal from a user. Reference numeral 321 indicates an HDD acting as a main storage unit for storing a drive program and collected data. Reference numeral 322 indicates an auxiliary storage unit for installing a temporary program.

Reference numeral 323 indicates a serial port (i.e., a PC interfacing port) acting as a connector connected to an external device such as a computer. Reference numeral 324 indicates an external printer port acting as a connector for standard printer connection. Reference numeral 325 indicates a power-supply unit for providing individual components with a power-supply signal to operate individual components.

In this case, the microprocessor 300 can transmit a signal at a frequency greater than 50 kHz to the transmission/reception probe 100 in order to measure a small-sized defect having a diameter 5 cm or less. The microprocessor 300 converts an analog frequency signal received via the reception probes 200 and the transmission/reception probe 100 into a digital signal, analyzes the digital signal, and outputs the analyzed result using the output unit.

The microprocessor 300 is shown in FIG. 3b. Referring to FIG. 3b, reference numeral 361 indicates a power-supply connector for receiving a power-supply signal from an external part. Reference numeral 362 indicates a pulley connector connected to the pulley of a measurement depth controller 500 to receive a pulley trigger signal 301. Reference numeral 363 indicates a transmitter connecter, which is connected to the transmission/reception probe 100, and transmits a control signal for starting ultrasound generation. Reference numeral 364 indicates a receiver connector, which is connected to the reception probe 200, and receives ultrasound information such as ultrasound speed received via the reception probe 200. Reference numeral 365 indicates a connector for increasing the number of preliminary receptions. The connector 365 is connected to the remaining receivers other than the reception probe 200 connected to a receiver connector 364 when a plurality of reception probes 200 are used, and receives speed and energy information of received ultrasound.

Reference numeral 366 indicates a thermal printer (i.e., an output unit 400) used to output data in an inspection field. Reference numeral 367 indicates a key entry unit for receiving a control signal from a user. Reference numeral 368 indicates a parallel port connected to an external device such as a computer. Reference numeral 369 indicates a serial port connected to the external device. Reference numeral 370 indicates a connector connected to an LCD screen. Reference numeral 371 indicates an indicator lamp for indicating a system operation state.

Reference numeral 372 indicates a display such as an LCD screen (i.e., the output unit 400) for displaying a variety of control signals entered by a user and an inspection result. Reference numeral 373 indicates a connection cable for connecting the display 372 to a main body. Reference numeral 374 indicates a cable storage room for storing cables connected to an external computer.

In this case, the microprocessor is not limited to the above-mentioned internal and external configurations, and it can be configured in the form of a variety of shapes as necessary.

The reception probe 200 is shown in FIG. 4b. Referring to FIG. 4b, reference numeral 271 indicates a nonconductor. The nonconductor 271 indicates a hollow plastic pipe body capable of transmitting ultrasound even underwater. Reference numeral 272 indicates a piezoelectric element positioned in a hole of the plastic pipe body 271, such that the piezoelectric element 272 can generate a voltage-variable signal according to externally received ultrasound. The piezoelectric element 272 is configured in the form of a cylinder so that it can receive ultrasound from all horizontal directions of 360°.

Reference numeral 273 indicates a metallic balance weight screwed to a lower part of the plastic pipe body 271, such that a desired object can be freely inserted into a vertical hole. Reference numeral 274 indicates a connector for external connection. The connector 274 is screwed to an upper part of the plastic pipe body 271 to fill the hole, and supports the piezoelectric element 272. Reference numeral 275 indicates a PCB (Printed Circuit Board). The PCB 275 is connected to the connector 274, amplifies the voltage-variable signal received from the piezoelectric element 272, and transmits the amplified voltage-variable signal. In this case, the PCB 275 includes a voltage amplifier 275A, a resistor 265B for determining an amplification factor, a capacitor 275C for voltage stabilization, and a voltage/current converter 275D.

Reference numeral 276 indicates insulation oil or thermosetting urethane, and it is also called a first filling material. The insulating oil transmits ultrasound received in the plastic pipe body 271 to the piezoelectric element 272, and fills the hole of the plastic pipe body 271 to prevent individual circuits from electric short-circuiting. The thermosetting urethane is solidified after the lapse of a predetermined time. Reference numeral 277 indicates an O-ring for sealing a connection part between the plastic pipe body 271 and the connector 274 to prevent water contained in a vertical hole from flowing in the plastic pipe body 271. Reference numeral 278 indicates a screw thread, which is formed on the circumference of the connector 274, and is connected to an external cable connector (not shown).

The transmission/reception probe 100 is shown in FIG. 4a. In this case, the transmission/reception probe 100 can transmit ultrasound, and can also receive reflected ultrasound. Basically, the transmission/reception probe 100 includes the above-mentioned reception probe 200. In more detail, the transmission/reception probe 100 includes structural components 171~178 corresponding to structural components 271~278 of the above-mentioned reception probe 200. The transmission/reception probe 100 further includes a piezoelectric element 162, an acrylic material 166, and an electric wire 165.

Reference numeral 162 indicates a piezoelectric element, which is positioned in the hole of the plastic pipe body 171, and horizontally generates ultrasound according to an external voltage-varied signal. The piezoelectric element 162 is configured in the form of a cylinder so that it can generate ultrasound in all horizontal directions of 360°.

Reference numeral 165 indicates an electric wire connected to the connector 174, such that the electric wire 165 transmits an external voltage to the piezoelectric element 162. A hole of the plastic pipe body 171 is filed with thermosetting urethane to transmit the ultrasound generated from the piezoelectric element 162 to the plastic pipe body 171.

In the meantime, as can be seen from FIG. 4, a reception piezoelectric element 172 and a transmission piezoelectric element 162 contained in the transmission/reception probe 100 are protected by different cases 176 and 166, respectively, the reception piezoelectric element 172 and the transmission piezoelectric element 162 can also be protected by only one case. In this case, in the case of the above-mentioned former and latter cases, the electric wire 165 for supporting the transmission piezoelectric element 162 is spaced apart from the reception piezoelectric element 172 and the PCB 175, and is fixed to prevent the reception piezoelectric element 172 and the PCB from being affected by the transmission piezoelectric element 162.

Figure 5:
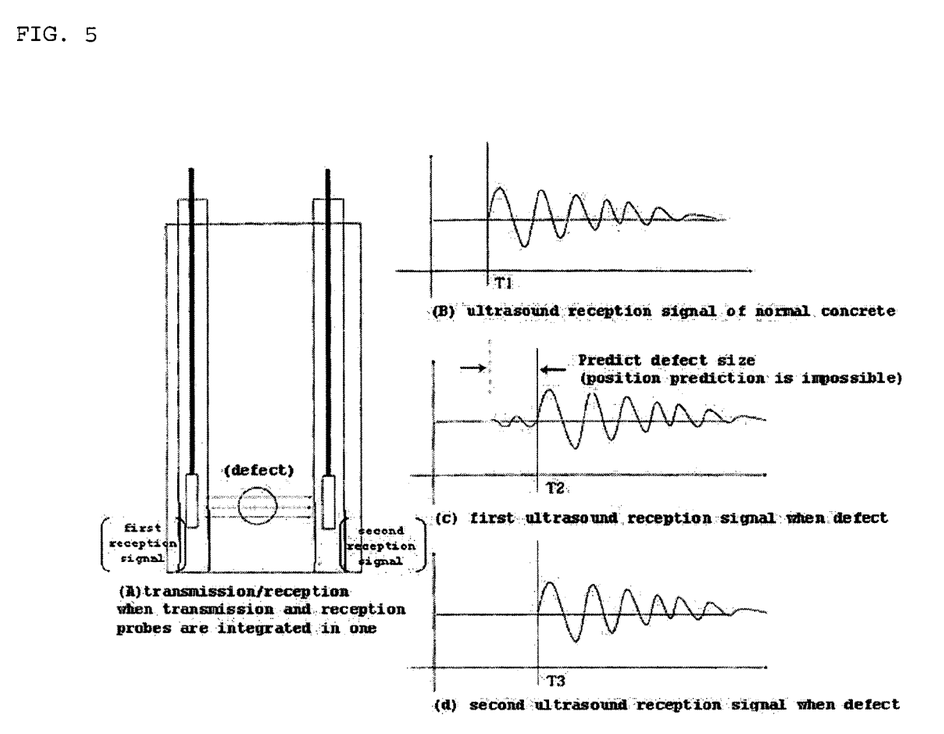
FIG. 5 shows a reception waveform of a transmission/reception probe and a reception probe for use in the nondestructive testing apparatus according to the present invention.

FIG. 5 shows a reception waveform of a transmission/reception probe and a reception probe for use in the nondestructive testing apparatus according to the present invention.

As described above, the present invention analyzes an ultrasound signal received from a plurality of reception probes 200 after being generated from the transmission/reception probe 100, and also analyzes a reflected ultrasound signal received in the transmission/reception probe 100 after being reflected from an object due to the occurrence of a defect, such that it can more precisely analyze position and size information of the defect on the basis of the analyzed result.

Namely, the present invention uses the transmission/reception probe 100 in which a reception probe is inserted into the transmission/reception probe, whereas transmission/reception probes for use in conventional nondestructive testing apparatuses (See Korean Patent No. 0439334) can only transmit ultrasound, such that it can provide data capable of analyzing a defect in three dimensions.

For example, as shown in FIG. 5, provided that a first signal received in the transmission/reception probe 100 is called a first reception signal, and a second signal received in the reception probe 200 is called a second reception signal, if the microprocessor 300 analyzes the first reception signal and the second reception signal after the first and second reception signals have been reflected, an ultrasound transmission time and a correct ultrasound arrival time from an ultrasound transmission time to an ultrasound reception time can be predicted, so that concrete homogeneity can also be predicted. In other words, the present invention implements the reflected result of the first reception signal with tomography, such that it can predict position, size, and other characteristics of a defect. Furthermore, the present invention can predict the concrete homogeneity on the basis of the result of the second reception signal. If the result of the first reception signal is combined with the result of the second reception signal, a concrete internal defect can be visually processed in three dimensions.

Figure 6:
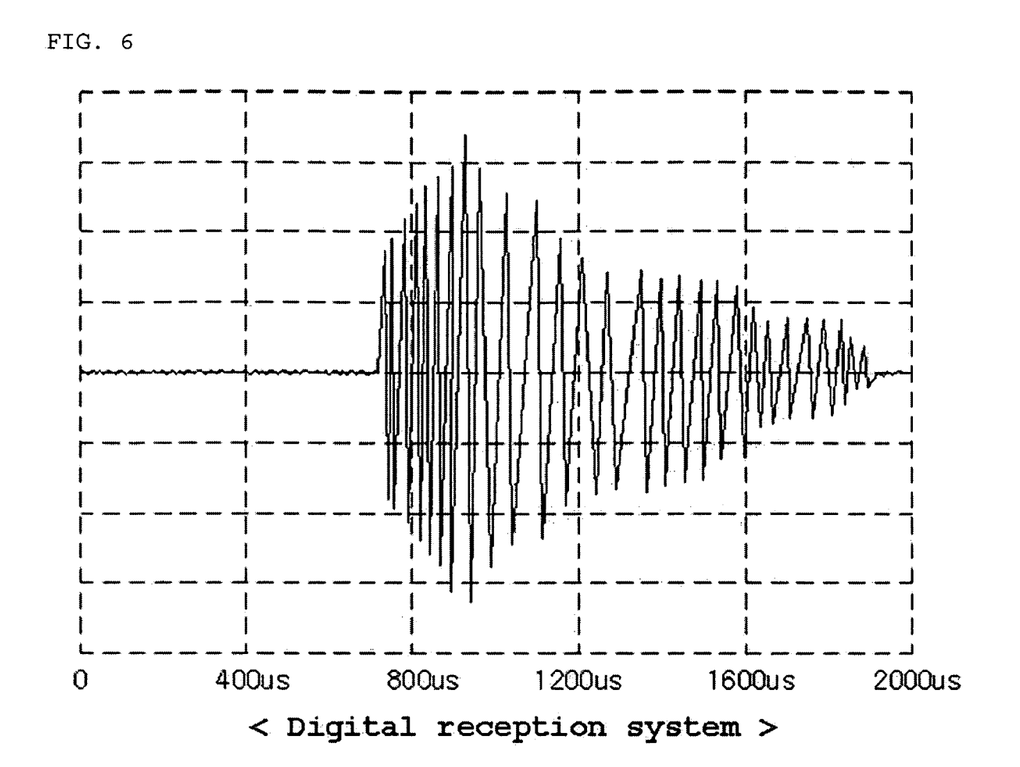
FIG. 6 is an exemplary display image of the nondestructive testing apparatus according to the present invention.

FIG. 6 is an exemplary display image of the nondestructive testing apparatus according to the present invention. In more detail, FIG. 6 shows an exemplary ultrasound reception signal generated from the output unit 400.

Since the conventional nondestructive testing apparatus is unable to recognize a horizontal length of the defect and energy variation, the present invention adds a converter for converting an analog signal into a digital signal to the microprocessor 300, and implements a digital tomography program, such that it can solve the above problem of the conventional nondestructive testing apparatus. According to the present invention, the microprocessor 300 sets the value of a division per display area of the output unit 400 to 400 µs (maximally, 500 µs), and transmits the division to the output unit 400, such that it can perform a division control denoted by 400 µs×5=2000 µs (maximally, 500 µs×5=2500 µs) using the switching unit and the program. The value of the division can be continuously adjusted by software. As a result, a concrete internal defect of a large-diameter placing pile having a diameter of more than 1.5 M can be detected and measured.

In the meantime, the above-mentioned application can be used to three-dimensionally predict homogeneity and defect positions of a variety of concrete structures (e.g., a placing pile, and a concrete partition, etc) having a very long ultrasound arrival time.

Figure 7:
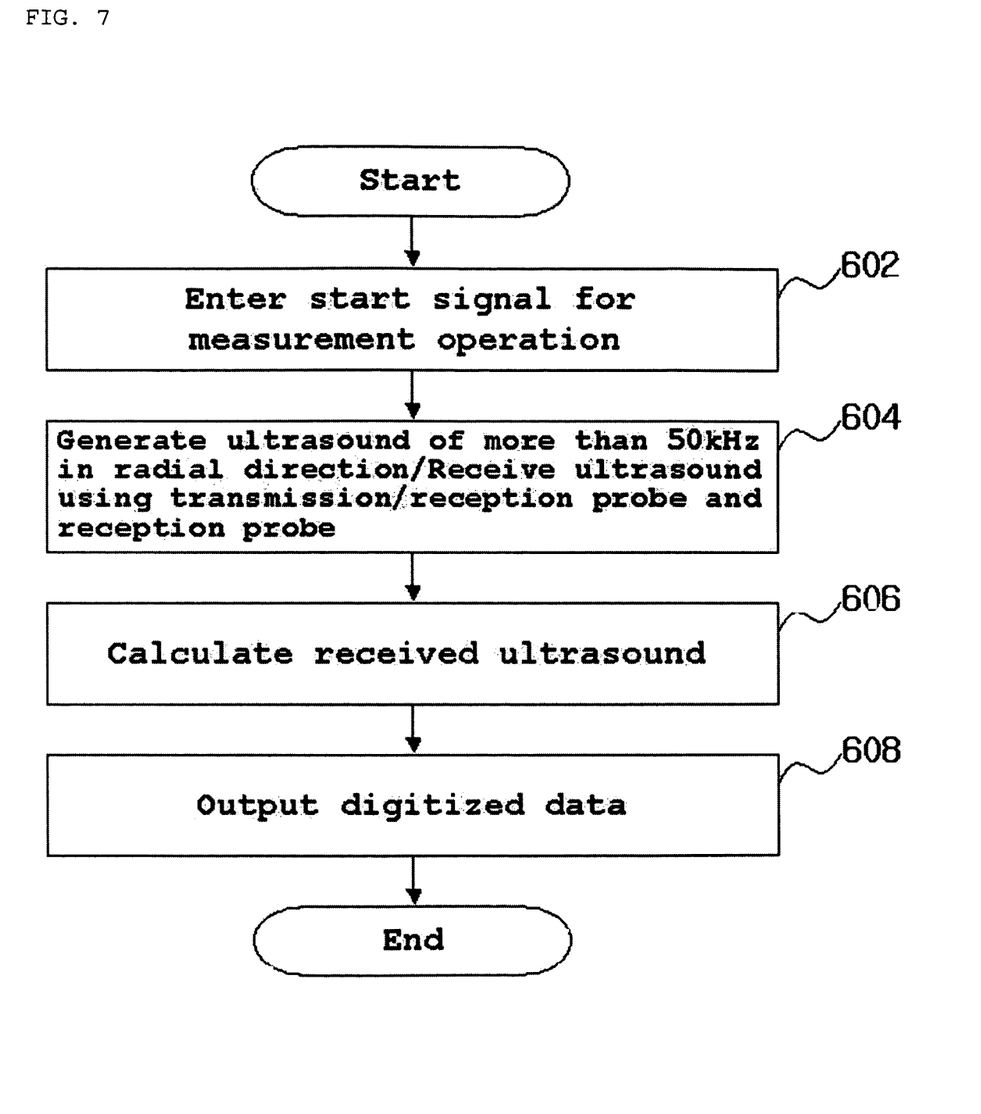
FIG. 7 is a flow chart illustrating an inspection method using the nondestructive testing apparatus according to the present invention.

FIG. 7 is a flow chart illustrating an inspection method using the nondestructive testing apparatus according to the present invention.

When constructing the concrete structure such as a concrete placing pile, the present invention must previously form a plurality of vertical holes, in which the transmission/reception probe 100 and the reception probe 200 are inserted, in an overall range of the concrete structure.

A user connects the transmission/reception probe 100 to the transmitter connector 363, and inserts the transmission/reception probe 100 into a vertical hole of the placing pile. Also, the user connects a plurality of reception probes 200 to the receiver connector 364 and the preliminary reception connector 365, and inserts them into different vertical holes of the placing pile, respectively.

After performing the above-mentioned operations, the user performs measurement operation setup using the key entry units 320 and 367, and enters an operation start signal at step S602. In this case, a pulley of the measurement depth controller (not shown) for allowing the transmission/reception probe 100 and the reception probes 200 to be maintained at the same depth in a vertical hole is connected to the pulley connector 362, and receives the pulley trigger signal 301, such that the pulley ascends or descends the transmission/reception probe 100 and the reception probes 200 by a predetermined measurement distance.

After the transmission/reception probe 100 and the reception probes 200 have ascended or descended, the transmission/reception probe 100 generates an ultrasound signal of more than 50 kHz in a radial direction upon receiving a control signal from the microprocessor 300. Each reception probe 200 and the transmission/reception probe 100 receive an ultrasound signal passing through the placing pile or the ultrasound signal reflected by an internal defect at step S604.

In this case, the main board 318 of the microprocessor 300 receives output signals of the transmission/reception probe 100 and the reception probe 200, and calculates ultrasound speed at step S606. In other words, a time consumed for receiving the ultrasound after the ultrasound has been generated is differently determined according to an internal state of the placing pile, such that a user can determine whether a defect occurs in the placing pile on the basis of the analyzed ultrasound speed.

The above-mentioned steps S602~S606 are repeated whenever the transmission/reception probe 100 and the reception probe 200 ascend or descend by the measurement depth controller (not shown) at intervals of a predetermined distance, in such a way that desired data can be collected.

The main board 118 converts ultrasound information received in each reception probe 200 into digital ultrasound information, collects the above-mentioned information, forms a single waveform associated with each cross section of the concrete structure on the basis of the collected information, and displays the waveform on the output units 400, 319, and 372, such that the user can easily recognize a defective part having poor quality. Also, the main board 118 transmits data to the thermal printer 366 via the printer controller 314 and the thermal printer port 315, and outputs the data in the form of a document, such that a user can recognize a defective part having poor quality at step S608.

The data calculated by the above-mentioned steps is stored in the main storage unit 321, and is re-loaded on the output units 400, 319, and 372 upon receiving a request from the user, such that the user can freely view the data. The data is transmitted to the external printer and the computer via the parallel port 368 and the serial port 369 connected to the external computer, such that the external printer and the computer can share the data with each other.

As apparent from the above description, a nondestructive testing apparatus according to the present invention inserts a transmission/reception probe and a reception probe in a vertical hole of a concrete structure such as a placing pile, and thus easily inspects an inaccessible part. The nondestructive testing apparatus controls the transmission/reception probe to generate ultrasound in a radial direction of 360°, and simultaneously receives the ultrasound using a plurality of reception probes and the transmission/reception probe, such that it can inspect quality of all parts of the concrete structure using only one process, resulting in reduction of a working time. Also, the nondestructive testing apparatus can correctly analyze position and size information of a defect of the concrete structure using a three-dimensional method.

The nondestructive testing apparatus uses ultrasound of more than 50 kHz, so that it can measure a small-sized defect having a diameter of 5 cm or less.

Furthermore, the nondestructive testing apparatus digitally processes the received ultrasound, and increases a gain of an output image, such that it can easily measure even an inner defect of the large-diameter concrete structure having a diameter 1.5 M and over.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. A nondestructive testing apparatus, comprising:
   (a) a transmission/reception probe which is inserted into a hole formed in a partition of a concrete structure, generates ultrasound of more than 50 KHz in a radial direction of 360°, and receives the reflected ultrasound after the ultrasound is reflected, wherein the transmission/reception probe includes:
      a hollow plastic pipe body formed of a nonconductor, for transmitting the ultrasound underwater;
      a first piezoelectric element positioned in a hole of the plastic pipe body; for generating a voltage-variable signal according to an external ultrasound signal;
      a metallic balance weight which is screwed to a lower part of the plastic pipe body, and is freely inserted into a vertical hole;
      an external connector which is screwed to an upper part of the plastic pipe body to fill the hole, and supports the piezoelectric element;
      a Printed Circuit Board (PCB) connected to the external connector, for amplifying the voltage-variable signal received from the piezoelectric element, and transmitting the amplified voltage-variable signal;
      a first filling material for transmitting the ultrasound received in the plastic pipe body to a piezoelectric element, and filling the hole of the plastic pipe body to prevent individual internal circuits from electric short-circuiting;
      an O-ring for sealing a connection part between the plastic pipe body and the connector to prevent water contained in the hole from flowing in the plastic pipe body;
      a screw thread which is formed on the circumference of the external connector, and is connected to an external cable connector;
      a second piezoelectric element which is positioned in a hole of the plastic pipe body, and generates an ultrasound signal in a radial direction of 360° according to an external voltage-variable signal;
      an electric wire connected to the external connector to transmit a voltage signal received from an external part to the second piezoelectric element; and
      a second filling material for filling the hole of the plastic pipe body to transmit the ultrasound generated from the piezoelectric element to the plastic pipe body,
      wherein the PCB includes a voltage amplifier, a resistor for determining an amplification factor, a capacitor for voltage stabilization, and a voltage/current converter which is configured in the form of a cylinder so that it can receive ultrasound from all horizontal directions of 360°;
   (b) a plurality of reception probes inserted in vertical holes different from that of the transmission/reception probe at the same depth in order to receive the ultrasound from the concrete partition;
   (c) a measurement depth controller for allowing the transmission/reception probe and the reception probes to maintain the same depth;
   (d) a microprocessor for controlling the measurement depth controller, converting information of the ultrasound received from the transmission/reception probe and the reception probes into digital ultrasound information, analyzing the digital ultrasound information, and determining density and quality of the concrete structure; and
   (e) an output unit for displaying various information analyzed by the microprocessor to allow a user to view the displayed information, and outputting the analyzed information.

2. The nondestructive testing apparatus according to claim 1, wherein the microprocessor converts the ultrasound information into a digital signal, such that the ultrasound information collected by the transmission/reception probe and the reception probes can be analyzed under a predetermined condition in which an overall time division is set to 2500 μs or less, or can be transmitted to the output unit.

* * * * *